US010780031B2

(12) United States Patent
Budde et al.

(10) Patent No.: US 10,780,031 B2
(45) Date of Patent: Sep. 22, 2020

(54) ABRASIVE CLEANING COMPOSITION (71) Applicant: Omya International AG, Oftringen (CH)

(72) Inventors: Tanja Budde, Zofingen (CH); Michael Skovby, Meilen (CH); Daniel E. Gerard, Basel (CH)

(73) Assignee: Omya International AG, Blue Ash, OH (US)

( * ) Notice: Subject to any disclaimer, the term of this patent is extended or adjusted under 35 U.S.C. 154(b) by 0 days.

(21) Appl. No.: 15/031,799

(22) PCT Filed: Dec. 12, 2014

(86) PCT No.: PCT/EP2014/077550
§ 371 (c)(1),
(2) Date: Apr. 25, 2016

(87) PCT Pub. No.: WO2015/086815
PCT Pub. Date: Jun. 18, 2015

(65) Prior Publication Data
US 2016/0271025 A1 Sep. 22, 2016

(30) Foreign Application Priority Data

Dec. 13, 2013 (EP) ..................... 13197113

(51) Int. Cl.
*A61K 8/19* (2006.01)
*A61Q 11/00* (2006.01)
*C11D 3/14* (2006.01)
*A61K 8/02* (2006.01)
*A61K 8/25* (2006.01)
*C11D 7/02* (2006.01)

(52) U.S. Cl.
CPC .............. *A61K 8/19* (2013.01); *A61K 8/022* (2013.01); *A61K 8/25* (2013.01); *A61Q 11/00* (2013.01); *C11D 3/14* (2013.01); *A61K 2800/28* (2013.01); *A61K 2800/413* (2013.01); *C11D 7/02* (2013.01)

(58) Field of Classification Search
CPC ............ B31F 1/12; D21H 19/00; D21H 17/67
USPC ....................................... 162/111
See application file for complete search history.

(56) References Cited

U.S. PATENT DOCUMENTS

| 4,209,504 | A | * | 6/1980 | Harth | ........ A61K 8/26 424/49 |
| 4,940,513 | A | * | 7/1990 | Spendel | ......... D21H 17/28 162/112 |
| 5,164,172 | A | | 11/1992 | Katayama et al. | |
| 2003/0031632 | A1 | | 2/2003 | Kiji et al. | |
| 2004/0020410 | A1 | | 2/2004 | Gane et al. | |
| 2004/0120902 | A1 | | 6/2004 | Wernett et al. | |
| 2009/0202451 | A1 | | 8/2009 | Prencipe et al. | |
| 2009/0321026 | A1 | * | 12/2009 | Medoff | ........ D21B 1/02 162/50 |
| 2012/0031576 | A1 | * | 2/2012 | Gane | ....... C09C 1/021 162/111 |
| 2012/0052023 | A1 | | 3/2012 | Gane et al. | |
| 2012/0186492 | A1 | | 7/2012 | Gane et al. | |

FOREIGN PATENT DOCUMENTS

| EP | 0219483 | A2 | 4/1987 | |
| EP | 2070991 | A1 | 6/2009 | |
| EP | 2684916 | A1 | 1/2014 | |
| EP | 2719373 | A1 | 4/2014 | |
| EP | 2883573 | A1 | 6/2015 | |
| EP | 2883573 | B1 | 10/2017 | |
| GB | 231987 | | 4/1925 | |
| JP | H07-118011 | A | 5/1995 | |
| JP | H07118011 | A | 5/1995 | |
| WO | 0010520 | A1 | 3/2000 | |
| WO | 0039222 | A1 | 7/2000 | |
| WO | 02085319 | A1 | 10/2002 | |
| WO | 03075874 | A1 | 9/2003 | |
| WO | 2007137606 | A1 | 12/2007 | |
| WO | WO2008113839 | * | 9/2008 | ............... D21C 9/08 |
| WO | 2009040597 | A1 | 4/2009 | |
| WO | 2009133173 | A1 | 11/2009 | |
| WO | 2010037753 | A1 | 4/2010 | |
| WO | WO2010037753 | * | 4/2010 | ............... A61K 9/14 |
| WO | 2010068442 | A1 | 6/2010 | |
| WO | 2013041419 | A1 | 3/2013 | |
| WO | 2013041711 | A2 | 3/2013 | |
| WO | 2013078949 | A1 | 6/2013 | |
| WO | WO-2015086815 | A1 | 6/2015 | |

OTHER PUBLICATIONS

The International Search Report dated Mar. 17, 2015 for PCT Application No. PCT/EP2014/077550.
The Written Opinion of International Searching Authority dated Mar. 17, 2015 for PCT Application PCT/EP2014/077550.
Office Action dated Oct. 7, 2016 for AU 2014363407.
Office Action dated Mar. 22, 2016 for BD/P/2014/278.
Office Action dated Dec. 21, 2016 for NZ 720219.
English Translation of Examination Report for TW 103141574.
Search Report dated Jun. 20, 2014 for EP 13197113.7.
International Preliminary Report on Patentability dated Jun. 23, 2016 for PCT/EP2014/077550.
Office action dated Mar. 7, 2017 for Canadian Application No. 2,928,799.
Office action dated Jun. 15, 2017 for Chilean Application No. 201601383.

(Continued)

*Primary Examiner* — Walter E Webb
(74) *Attorney, Agent, or Firm* — Schwegman Lundberg & Woessner, P.A.

(57) ABSTRACT

The present invention relates to an abrasive cleaning composition comprising at least 6 wt.-%, based on the total weight of the composition, of a surface-reacted calcium carbonate as an abrasive material, wherein the surface-reacted calcium carbonate is a reaction product of natural or synthetic calcium carbonate with carbon dioxide and at least one acid.

26 Claims, 1 Drawing Sheet (56) References Cited

OTHER PUBLICATIONS

Office action dated Jan. 24, 2018 for Chinese Application No. 201480068222.5.
Office action dated Nov. 3, 2017 for Colombian Application No. 16154021.
Office action dated Jun. 16, 2017 for Korean Application No. 10-2016-7014488.
Office action dated Mar. 19, 2018 for Pakistani Application No. 869/2014.
Office action dated Nov. 20, 2017 for Russian Application No. 2016127915.
Office action dated Aug. 29, 2017 for Singapore Application No. 11201603559X.
Notice of Opposition dated Jul. 11, 2018 filed by Unilever NV in European Application No. EP 13197113.7.
Notice of Opposition Facts and Arguments dated Jul. 11, 2018 filed by Unilever NV in European Application No. EP 13197113.7.
EPO Communication of a Notice of Opposition dated Jul. 17, 2018 filed by Unilever NV in European Application No. EP 13197113.7.
Proprietor's Response to R. 70(2) and 70a(2) EPC dated Dec. 17, 2015 filed by Maiwald Patentanwaltsgesellschaft mbH in European Application No. EP 13197113.7.
Hinedi et al., "A 31P and 1H MAS NMR Study of Phosphate Sorption Onto Calcium Carbonate," Journal of Colloid and Interface Science, vol. 152, No. 1, Aug. 1992.
Hengchang, "Science of Dental Materials," Peking University Medical Press, 1st Edition, Aug. 2005, p. 214, (English translation consists of 2 pages).
Jiuwen, "Commercial Goods for Daily Use," Central Radio and Television University Press, Apr. 1984, p. 478, (English translation consists of 2 pages).
Examination Report dated May 27, 2018 for the Cooperation Council for the Arab States of the Gulf Application No. GC 2014-28525.
Office action dated Jul. 23, 2018 for Chinese Application No. 201480068222.5.
Office action dated Aug. 28, 2018 for Indian Application No. 201627019194.
"European Application Serial No. 13197113.7, Communication Pursuant to Article 94(3) EPC dated Apr. 29, 2016", 9 pgs.
"European Application Serial No. 13197113.7, Communication Pursuant to Article 94(3) EPC dated Nov. 24, 2016", 5 pgs.
"European Application Serial No. 13197113.7, Druckexemplar in opposition procedure mailed Feb. 4, 2020", 31 pgs.
"European Application Serial No. 13197113.7, Interlocutory decision in Opposition proceedings mailed Feb. 4, 2020", 23 pgs.
"European Application Serial No. 13197113.7, Minutes of the oral proceedings before the Opposition Division mailed Feb. 4, 2020", 8 pgs.
"European Application Serial No. 13197113.7, Office Action dated May 29, 2017", 8 pgs.
"European Application Serial No. 13197113.7, Response filed Feb. 3, 2017 to Communication Pursuant to Article 94(3) EPC dated Nov. 24, 2016", 92 pgs.
"European Application Serial No. 13197113.7, Response filed Sep. 1, 2016 to Communication Pursuant to Article 94(3) EPC dated Apr. 29, 2016", 18 pgs.
"European Application Serial No. 13197113.7, Response filed Oct. 4, 2019 to Summons to Attend Oral Proceedings mailed Apr. 2, 2019", 20 pgs.
"European Application Serial No. 13197113.7, Response filed Dec. 17, 2015 to Extended European Search Report dated Jun. 20, 2014", 13 pgs.
"European Application Serial No. 13197113.7, Scanned annex to communication—opposition procedure mailed Feb. 4, 2020", 25 pgs.
"European Application Serial No. 13197113.7, Summons to Attend Oral Proceedings mailed Apr. 2, 2019", 11 pgs.
"Machine translation of JPH 07118011", Espacenet.com, 3 pgs, Date; May 9, 1995.
"Precipitated calcium carbonate", Chu Shin Chemical Co, Ltd., [Online] Retrieved from the Internet: <URL: http://www.chu/shin.com/en/products01.html>, (Retrieved Nov. 30, 2018), 2 pgs.
"Proprietor response to R. 70(2) and 70a(2)", (Dec. 17, 2015), 13 pgs.
"Reproduction of examples 2,3 and 6 of 04", 5 pgs.

* cited by examiner

ABRASIVE CLEANING COMPOSITION

CROSS-REFERENCE TO RELATED APPLICATIONS

This is a U.S. national phase of PCT Application No. PCT/EP2014/077550, filed Dec. 12, 2014, which claims priority to European Application No. 13197113.7, filed Dec. 13, 2013.

The present invention relates to an abrasive cleaning composition, its use and a method for cleaning surfaces.

Abrasive cleaners are well-known in the art and are widely used for cleaning all kind of surfaces, especially surfaces which become soiled with difficulty to remove stains and soils. For example, abrasive cleaners may be used for cleaning household surfaces such as tables, sinks or dish surfaces, as well as in personal care products such as toothpastes, facial and body scrub, or soaps.

Conventional abrasive cleaners contain inorganic abrasives such as carbonate salts, clay, silica, silicate, shale ash, perlite or quartz sand, or organic polymer beads such as polypropylene, PVC, melamine, urea, polyacrylate or derivatives thereof. A liquid cleaning composition comprising calcium carbonate as abrasive material is, for example, described in WO 2013/078949. A dry blasting process for the cleaning of solid surfaces involving the use of natural alkaline earth carbonate particles is disclosed in WO 2009/133173.

Particulate calcium carbonate is a highly effective tough soil remover, but has also a high potential for surface damage. Therefore, it is problematic to use it for delicate surfaces. For example, if used in toothpaste, calcium carbonate-based abrasives can damage the enamel and the dentin of the teeth. Moreover, in order to create a pleasant feeling in the mouth conventional toothpastes require a high amount of calcium carbonate, which in turn, may lead to the unfavourable taste property of chalkiness.

In order to overcome some drawbacks of calcium carbonate-based abrasives, it was proposed to use surface coated calcium carbonate. WO 2013/041711 describes a powder for dental powder blasting, wherein the calcium carbonate particles are coated with alkali metal fluoride. WO 02/085319 is concerned with a fluoride compatible calcium carbonate, wherein the calcium carbonate particles have been treated with fatty acids and/or polysaccharides. A pyrophosphate coating process for calcium carbonate dental abrasives is disclosed in EP 0 219 483. WO 03/075874 relates to toothpaste compositions including acid resistant calcium carbonate, which has been surface treated with silicate. However, all these processes lead to calcium carbonate particles, wherein the originally porous surface of the calcium carbonate particle is sealed by the applied surface coating, and thus, the surface-structure is altered.

In view of the foregoing, there is a continuous need for new abrasives that can be employed in cleaning compositions.

Accordingly it is an object of the present invention to provide an abrasive cleaning composition, which avoids at least some of the foregoing disadvantages. In particular, it is desirable to provide an abrasive cleaning composition which has very gentle abrasive properties, and therefore, can also be used for cleaning delicate surfaces. It is also desirable that the abrasive material provides a pleasant mouthfeel when used in toothpastes.

Furthermore, it is an object of the present invention to provide an abrasive cleaning composition which is based on materials that can be obtained from natural sources. It is also desirable to provide a cleaning composition including abrasives which are easily biodegradable.

The foregoing and other objects are solved by the subject-matter as defined herein in the independent claims.

According to one embodiment of the present invention, an abrasive cleaning composition is provided comprising
at least 6 wt.-%, based on the total weight of the composition, of a surface-reacted calcium carbonate as an abrasive material,
wherein the surface-reacted calcium carbonate is a reaction product of natural or synthetic calcium carbonate with carbon dioxide and at least one acid.

According to another embodiment of the present invention, a method of cleaning a surface is provided, wherein the surface is contacted with an abrasive cleaning composition according to the present invention.

According to still another embodiment of the present invention, the use of a surface-reacted calcium carbonate as abrasive material is provided, wherein the surface-reacted calcium carbonate is a reaction product of natural or synthetic calcium carbonate with carbon dioxide and at least one acid.

According to still another embodiment of the present invention, the use of an abrasive cleaning composition according to the present invention for cleaning a surface is provided.

Advantageous embodiments of the present invention are defined in the corresponding sub-claims.

According to one embodiment the composition further comprises at least one additional abrasive material, preferably selected from the group consisting of silica, precipitated silica, alumina, aluminosilicate, metaphosphate, tricalcium phosphate, calcium pyrophosphate, natural ground calcium carbonate, precipitated calcium carbonate, sodium bicarbonate, bentonite, kaolin, aluminium hydroxide, calcium hydrogen phosphate, hydroxylapatite, and mixtures thereof. According to another embodiment the at least one acid is selected from the group consisting of hydrochloric acid, sulphuric acid, sulphurous acid, phosphoric acid, citric acid, oxalic acid, acetic acid, formic acid, and mixtures thereof, wherein preferably the at least one acid is phosphoric acid.

According to one embodiment the surface-reacted calcium carbonate is in form of particles having a weight median particle size $d_{50}$ from 0.1 to 100 µm, preferably from 0.5 to 50 µm, more preferably from 1 to 20 µm, even more preferably from 2 to 10 µm, and most preferably from 5 to 10 µm. According to another embodiment the composition comprises from 10 to 80 wt.-%, preferably from 15 to 70 wt.-%, more preferably from 20 to 60 wt.-%, even more preferably from 25 to 50 wt.-%, and most preferably about 30 wt.-% of the surface-reacted calcium carbonate, based on the total weight of the composition.

According to one embodiment the composition is an oral care composition, preferably a toothpaste, a toothpowder, a powder for dental powder blasting or a chewable gum, and wherein preferably the surface-reacted calcium carbonate is a reaction product of natural or synthetic calcium carbonate with carbon dioxide and phosphoric acid. According to another embodiment the surface-reacted calcium carbonate has a radioactive dentin abrasion (RDA) value between 10 and 100, preferably between 30 and 70.

According to one embodiment the composition does not contain additional calcium carbonate-based materials. According to another embodiment the surface-reacted calcium carbonate comprises an insoluble, at least partially crystalline calcium salt of an anion of the at least one acid, which is formed on the surface of the natural or synthetic calcium carbonate. According to still another embodiment the composition further comprises a surfactant, preferably in an amount from 0.1 to 10 wt.-%, preferably from 0.5 to 8 wt.-%, and most preferably from 1 to 5 wt.-%, based on the total amount of the composition.

According to one embodiment the surface, which is contacted with the inventive composition, is an animate surface, preferably selected from the group consisting of human skin, animal skin, human hair, animal hair, and tissues of the oral cavity such as teeth, gums, tongue or buccal surfaces. According to another embodiment the surface-reacted calcium carbonate is used as dental abrasive material.

It should be understood that for the purpose of the present invention, the following terms have the following meaning.

The term "abrasive material" in the meaning of the present invention refers to a particulate substance that is capable of polishing or cleaning surfaces by rubbing or grinding. For determining the "abrasiveness" of the abrasive material, the methods described in the examples section can be used.

For the purpose of the present invention, an "acid" is defined as Brønsted-Lowry acid, that is to say, it is an $H_3O^+$ ion provider. An "acid salt" is defined as an $H_3O^+$ ion-provider that is partially neutralized by an electropositive element. A "salt" is defined as an electrically neutral ionic compound formed from anions and cations. A "partially crystalline salt" is defined as a salt that, on XRD analysis, presents an essentially discrete diffraction pattern.

A "carrier material" in the meaning of the present invention is a base material which can be combined with the abrasive cleaning composition of present invention and facilitates the application of the abrasive cleaning composition. Examples of carrier materials are toothpaste formulations, chewable gums, patches, creams, oils or soaps.

In the meaning of the present invention, the "radioactive dentin abrasion (RDA)" is a measure of the erosive effect of abrasives in toothpaste on tooth dentin. It involves using standardized abrasives compared against the test sample. The determination of this value is done by determining the activity while cleaning worn dentin which is radioactively marked by mild neutron irradiation. The values obtained depend on the size, quantity and surface structure of abrasive used in toothpastes. The RDA value is set by the standards DIN EN ISO 11609. The RDA values given in the examples section of the present invention are relative RDA values, which have been measured and correlated to the aforementioned RDA values by the method described in the examples section.

For the purposes of the present invention, the term "gloss" refers to the ability of a substrate, for example, a glass or plastic plate, to reflect some portion of the incident light at the mirror angle. Gloss may be based on a measurement of the quantity of light specularly reflected from the surface of a substrate at a set angle of incidence, for example, at 20°, such as in the case of 20° gloss and is specified in percent. The gloss can be determined according to EN ISO 8254-1: 2003.

"Ground calcium carbonate" (GCC) in the meaning of the present invention is a calcium carbonate obtained from natural sources, such as limestone, marble, dolomite, or chalk, and processed through a wet and/or dry treatment such as grinding, screening and/or fractionating, for example, by a cyclone or classifier.

"Precipitated calcium carbonate" (PCC) in the meaning of the present invention is a synthesized material, obtained by precipitation following reaction of carbon dioxide and lime in an aqueous environment or by precipitation of a calcium and carbonate ion source in water. PCC may be in the vateritic, calcitic or aragonitic crystal form.

Throughout the present document, the "particle size" of a calcium carbonate material or abrasive material is described by its distribution of particle sizes. The value $d_x$ represents the diameter relative to which x % by weight of the particles have diameters less than $d_x$. This means that the $d_{20}$ value is the particle size at which 20 wt.-% of all particles are smaller, and the $d_{75}$ value is the particle size at which 75 wt.-% of all particles are smaller. The $d_{50}$ value is thus the weight median particle size, i.e. 50 wt.-% of all grains are bigger or smaller than this particle size. For the purpose of the present invention the particle size is specified as weight median particle size $d_{50}$ unless indicated otherwise. For determining the weight median particle size $d_{50}$ value a Malvern Mastersizer 2000, can be used.

A "specific surface area (SSA)" of a calcium carbonate in the meaning of the present invention is defined as the surface area of the mineral pigment divided by the mass of the calcium carbonate. As used herein, the specific surface area is measured by nitrogen gas adsorption using the BET isotherm (ISO 9277:2010) and is specified in $m^2/g$.

In the meaning of the present invention, the term "surfactant" refers to a compound that lowers the surface tension or interfacial tension between two liquids or between a liquid and a solid, and may act as detergent, wetting agent, emulsifier, foaming agent, or dispersant.

For the purpose of the present invention, the term "viscosity" or "Brookfield viscosity" refers to Brookfield viscosity. The Brookfield viscosity is for this purpose measured by a Brookfield (Typ RVT) viscometer at 20° C.±2° C. at 100 rpm using an appropriate spindle and is specified in mPa·s.

A "suspension" or "slurry" in the meaning of the present invention comprises insoluble solids and water, and optionally further additives and usually contains large amounts of solids and, thus, is more viscous and can be of higher density than the liquid from which it is formed.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group, which preferably consists only of these embodiments.

Where an indefinite or definite article is used when referring to a singular noun, e.g. "a", "an" or "the", this includes a plural of that noun unless something else is specifically stated.

Terms like "obtainable" or "definable" and "obtained" or "defined" are used interchangeably. This e.g. means that, unless the context clearly dictates otherwise, the term "obtained" does not mean to indicate that e.g. an embodiment must be obtained by e.g. the sequence of steps following the term "obtained" though such a limited understanding is always included by the terms "obtained" or "defined" as a preferred embodiment.

The inventive abrasive cleaning composition comprises at least 6 wt.-%, based on the total weight of the composition, of a surface-reacted calcium carbonate as an abrasive material. The surface-reacted calcium carbonate is a reaction product of natural or synthetic calcium carbonate with carbon dioxide and at least one acid.

In the following the details and preferred embodiments of the inventive composition will be set out in more details. It is to be understood that these technical details and embodiments also apply to the inventive use of the composition, the inventive use of the surface-reacted calcium carbonate as well as to the inventive method.

The Surface-Reacted Calcium Carbonate

According to the present invention, the surface-reacted calcium carbonate is a reaction product of natural or synthetic calcium carbonate with carbon dioxide and at least one acid.

Natural (or ground) calcium carbonate (GCC) is understood to be a naturally occurring form of calcium carbonate, mined from sedimentary rocks such as limestone or chalk, or from metamorphic marble rocks. Calcium carbonate is known to exist as three types of crystal polymorphs: calcite, aragonite and vaterite. Calcite, the most common crystal polymorph, is considered to be the most stable crystal form of calcium carbonate. Less common is aragonite, which has a discrete or clustered needle orthorhombic crystal structure. Vaterite is the rarest calcium carbonate polymorph and is generally unstable. Natural calcium carbonate is almost exclusively of the calcitic polymorph, which is said to be trigonal-rhombohedral and represents the most stable of the calcium carbonate polymorphs. The term "source" of the calcium carbonate in the meaning of the present invention refers to the naturally occurring mineral material from which the calcium carbonate is obtained. The source of the calcium carbonate may comprise further naturally occurring components such as magnesium carbonate, alumino silicate etc.

According to one embodiment of the present invention, the natural calcium carbonate is selected from the group consisting of marble, chalk, dolomite, limestone and mixtures thereof.

According to one embodiment of the present invention the GCC is obtained by dry grinding. According to another embodiment of the present invention the GCC is obtained by wet grinding and optionally subsequent drying.

In general, the grinding step can be carried out with any conventional grinding device, for example, under conditions such that comminution predominantly results from impacts with a secondary body, i.e. in one or more of: a ball mill, a rod mill, a vibrating mill, a roll crusher, a centrifugal impact mill, a vertical bead mill, an attrition mill, a pin mill, a hammer mill, a pulveriser, a shredder, a de-clumper, a knife cutter, or other such equipment known to the skilled man. In case the calcium carbonate containing mineral material comprises a wet ground calcium carbonate containing mineral material, the grinding step may be performed under conditions such that autogenous grinding takes place and/or by horizontal ball milling, and/or other such processes known to the skilled man. The wet processed ground calcium carbonate containing mineral material thus obtained may be washed and dewatered by well-known processes, e.g. by flocculation, filtration or forced evaporation prior to drying. The subsequent step of drying may be carried out in a single step such as spray drying, or in at least two steps. It is also common that such a mineral material undergoes a beneficiation step (such as a flotation, bleaching or magnetic separation step) to remove impurities.

"Precipitated calcium carbonate" (PCC) in the meaning of the present invention is a synthesized material, generally obtained by precipitation following reaction of carbon dioxide and lime in an aqueous environment or by precipitation of a calcium and carbonate ion source in water or by precipitation of calcium and carbonate ions, for example $CaCl_2$ and $Na_2CO_3$, out of solution. Further possible ways of producing PCC are the lime soda process, or the Solvay process in which PCC is a by-product of ammonia production. Precipitated calcium carbonate exists in three primary crystalline forms: calcite, aragonite and vaterite, and there are many different polymorphs (crystal habits) for each of these crystalline forms. Calcite has a trigonal structure with typical crystal habits such as scalenohedral (S-PCC), rhombohedral (R-PCC), hexagonal prismatic, pinacoidal, colloidal (C-PCC), cubic, and prismatic (P-PCC). Aragonite is an orthorhombic structure with typical crystal habits of twinned hexagonal prismatic crystals, as well as a diverse assortment of thin elongated prismatic, curved bladed, steep pyramidal, chisel shaped crystals, branching tree, and coral or worm-like form. Vaterite belongs to the hexagonal crystal system. The obtained PCC slurry can be mechanically dewatered and dried.

According to one embodiment of the present invention, the synthetic calcium carbonate is precipitated calcium carbonate, preferaby comprising aragonitic, vateritic or calcitic mineralogical crystal forms or mixtures thereof.

According to one embodiment of the present invention, the natural or synthetic calcium carbonate is ground prior to the treatment with carbon dioxide and at least one acid. The grinding step can be carried out with any conventional grinding device such as a grinding mill known to the skilled person.

Preferably the surface-reacted calcium carbonate to be used in the present invention is prepared as an aqueous suspension having a pH, measured at 20° C., of greater than 6.0, preferably greater than 6.5, more preferably greater than 7.0, even more preferably greater than 7.5.

In a preferred process for the preparation of the aqueous suspension of surface-reacted calcium carbonate, the natural or synthetic calcium carbonate, either finely divided, such as by grinding, or not, is suspended in water. Preferably, the slurry has a content of natural or synthetic calcium carbonate within the range of 1 wt.-% to 80 wt.-%, more preferably 3 wt.-% to 60 wt.-%, and even more preferably 5 wt.-% to 40 wt.-%, based on the weight of the slurry.

In a next step, at least one acid is added to the aqueous suspension containing the natural or synthetic calcium carbonate. According to one embodiment of the present invention, the at least one acid is selected from the group consisting of hydrochloric acid, sulphuric acid, sulphurous acid, phosphoric acid, citric acid, oxalic acid, acetic acid, formic acid, and mixtures thereof. Preferably the at least one acid is phosphoric acid. Without being bound to any theory, the inventors believe that the use of phosphoric acid can be beneficial if the surface-reacted calcium carbonate is employed in oral applications.

According to one embodiment, the at least one acid has a $pK_a$ at 25° C. of 2.5 or less. If the $pK_a$ at 25° C. is 0 or less, the acid is preferably selected from sulphuric acid, hydrochloric acid, or mixtures thereof. If the $pK_a$ at 25° C. is from 0 to 2.5, the acid is preferably selected from $H_2SO_3$, $HSO_4^-$, $H_3PO_4$, oxalic acid or mixtures thereof. The at least one acid can be added to the suspension as a concentrated solution or a more diluted solution. Preferably, the molar ratio of the at least one acid to the natural or synthetic calcium carbonate is from 0.05 to 4, more preferably from 0.1 to 2.

As an alternative, it is also possible to add the at least one acid to the water before the natural or synthetic calcium carbonate is suspended.

In a next step, the natural or synthetic calcium carbonate is treated with carbon dioxide. The carbon dioxide can be formed in situ by the acid treatment and/or can be supplied from an external source. If a strong acid such as sulphuric acid or hydrochloric acid is used for the acid treatment of the natural or synthetic calcium carbonate, the carbon dioxide is automatically formed. Alternatively or additionally, the carbon dioxide can be supplied from an external source.

Acid treatment and treatment with carbon dioxide can be carried out simultaneously which is the case when a strong acid is used. It is also possible to carry out acid treatment first, e.g. with a medium strong acid having a $pK_a$ in the range of 0 to 2.5, followed by treatment with carbon dioxide supplied from an external source.

Preferably, the concentration of gaseous carbon dioxide in the suspension is, in terms of volume, such that the ratio (volume of suspension):(volume of gaseous $CO_2$) is from 1:0.05 to 1:20, even more preferably from 1:0.05 to 1:5.

In a preferred embodiment, the acid treatment step and/or the carbon dioxide treatment step are repeated at least once, more preferably several times.

Subsequent to the acid treatment and carbon dioxide treatment, the pH of the aqueous suspension, measured at 20° C., naturally reaches a value of greater than 6.0, preferably greater than 6.5, more preferably greater than 7.0, even more preferably greater than 7.5, thereby preparing the surface-reacted natural or synthetic calcium carbonate as an aqueous suspension having a pH of greater than 6.0, preferably greater than 6.5, more preferably greater than 7.0, even more preferably greater than 7.5. If the aqueous suspension is allowed to reach equilibrium, the pH is greater than 7. A pH of greater than 6.0 can be adjusted without the addition of a base when stirring of the aqueous suspension is continued for a sufficient time period, preferably 1 hour to 10 hours, more preferably 1 to 5 hours.

Alternatively, prior to reaching equilibrium, which occurs at a pH greater than 7, the pH of the aqueous suspension may be increased to a value greater than 6 by adding a base subsequent to carbon dioxide treatment. Any conventional base such as sodium hydroxide or potassium hydroxide can be used.

Further details about the preparation of the surface-reacted natural calcium carbonate are disclosed in WO 00/39222 and US 2004/0020410, wherein the surface-reacted natural calcium carbonate is described as a filler for paper manufacture. The use of surface-reacted calcium carbonate as carrier for the controlled release of active agents is described in WO 2010/037753.

Similarly, surface-reacted precipitated calcium carbonate is obtained. As can be taken in detail from EP 2 070 991, surface-reacted precipitated calcium carbonate is obtained by contacting precipitated calcium carbonate with $H_3O^+$ ions and with anions being solubilised in an aqueous medium and being capable of forming water-insoluble calcium salts, in an aqueous medium to form a slurry of surface-reacted precipitated calcium carbonate, wherein said surface-reacted precipitated calcium carbonate comprises an insoluble, at least partially crystalline calcium salt of said anion formed on the surface of at least part of the precipitated calcium carbonate.

Said solubilised calcium ions correspond to an excess of solubilised calcium ions relative to the solubilised calcium ions naturally generated on dissolution of precipitated calcium carbonate by $H_3O^+$ ions, where said $H_3O^+$ ions are provided solely in the form of a counterion to the anion, i.e. via the addition of the anion in the form of an acid or non-calcium acid salt, and in absence of any further calcium ion or calcium ion generating source.

Said excess solubilised calcium ions are preferably provided by the addition of a soluble neutral or acid calcium salt, or by the addition of an acid or a neutral or acid non-calcium salt which generates a soluble neutral or acid calcium salt in situ.

Said $H_3O^+$ ions may be provided by the addition of an acid or an acid salt of said anion, or the addition of an acid or an acid salt which simultaneously serves to provide all or part of said excess solubilised calcium ions.

The surface-reacted calcium carbonate can be kept in suspension, optionally further stabilised by a dispersant. Conventional dispersants known to the skilled person can be used. A preferred dispersant is polyacrylic acid.

Alternatively, the aqueous suspension described above can be dried, thereby obtaining the solid (i.e. dry or containing as little water that it is not in a fluid form) surface-reacted natural or synthetic calcium carbonate in the form of granules or a powder.

According to one embodiment of the present invention, the surface-reacted calcium carbonate has a specific surface area of from 5 $m^2/g$ to 200 $m^2/g$, more preferably 20 $m^2/g$ to 80 $m^2/g$ and even more preferably 30 $m^2/g$ to 60 $m^2/g$, measured using nitrogen and the BET method according to ISO 9277.

According to one embodiment of the present invention, the surface-reacted calcium carbonate is in form of particles having a weight median particle size $d_{50}$ from 0.1 to 100 µm, preferably from 0.5 to 50 µm, more preferably from 1 to 20 µm, even more preferably from 2 to 10 µm, and most preferably from 5 to 10 µm.

According to one embodiment of the present invention, the surface-reacted calcium carbonate comprises an insoluble, at least partially crystalline calcium salt of an anion of the at least one acid, which is formed on the surface of the natural or synthetic calcium carbonate. Depending on the employed at least one acid, the anion may be sulphate, sulphite, phosphate, citrate, oxalate, acetate, formiate and/or chloride.

According to a further aspect of the present invention, the use of a surface-reacted calcium carbonate as abrasive material is provided, wherein the surface-reacted calcium carbonate is a reaction product of natural or synthetic calcium carbonate with carbon dioxide and at least one acid. The abrasive material can be employed in cleaning compositions, for example, household cleaners such as scouring creams or ceramic cook top cleaners, polishing pastes or creams, or cosmetic compositions such as body scrub or face peelings.

According to a preferred embodiment, the surface-reacted calcium carbonate is used as dental abrasive material. The dental abrasive material can be employed, for example, as abrasive material in toothpastes, toothpowders or chewing gums or as abrasive material in dental powder blasting.

The Abrasive Cleaning Composition

The abrasive cleaning composition of the present invention comprises at least 6 wt.-%, based on the total weight of the composition, of a surface-reacted calcium carbonate as an abrasive material. For example, the abrasive cleaning composition can comprise at least 7 wt.-%, at least 8 wt.-%, or at least 9 wt.-%, based on the total weight of the composition, of a surface-reacted calcium carbonate as an abrasive material. According to one embodiment of the present invention, the composition comprises from 10 to 80 wt.-%, preferably from 15 to 70 wt.-%, more preferably from 20 to 60 wt.-%, even more preferably from 25 to 50 wt.-%, and most preferably about 30 wt.-% of the surface-reacted calcium carbonate, based on the total weight of the composition.

The surface-reacted calcium carbonate can consist of only one type of surface-reacted calcium carbonate or can be a mixture of two or more types of surface-reacted calcium carbonate. The abrasive cleaning composition of the present invention may contain the surface-reacted calcium carbonate as the only abrasive material. Alternatively, the abrasive cleaning composition of the present invention may contain the surface-reacted calcium carbonate in combination with at least one additional abrasive material. The further abrasive material can be made from plastic, hard waxes, inorganic and organic abrasives, or natural materials.

According to one embodiment the abrasive cleaning composition of the present invention, further comprises at least one additional abrasive material. Preferably the additional abrasive material is selected from the group consisting of silica, precipitated silica, alumina, aluminosilicate, metaphosphate, tricalcium phosphate, calcium pyrophosphate, natural ground calcium carbonate, precipitated calcium carbonate, sodium bicarbonate, bentonite, kaolin, aluminium hydroxide, calcium hydrogen phosphate, hydroxylapatite, and mixtures thereof. According to a preferred embodiment, the additional abrasive material is selected from ground calcium carbonate and/or precipitated silica. According to another preferred embodiment, the at least one additional abrasive material is selected from the group consisting of natural calcium carbonate, precipitated calcium carbonate, aluminium hydroxide, calcium hydrogen phosphate, silica, hydroxylapatite, and mixtures thereof.

According to one embodiment, the additional abrasive material has a weight median particle size $d_{50}$ from 0.1 to 100 μm, preferably from 0.5 to 50 μm, more preferably from 1 to 20 μm, and most preferably from 2 to 10 μm.

The at least one additional abrasive material can be present in the abrasive cleaning composition in an amount from 1 to 80 wt.-%, based on the total weight of the composition, preferably from 5 to 70 wt.-%, more preferably from 10 to 60 wt.-%, and most preferably from 20 to 50 wt.-%.

According to a preferred embodiment, the abrasive cleaning composition comprises at least 6 wt.-% of a surface-reacted calcium carbonate as abrasive material and from 1 to 80 wt.-% of an additional abrasive material, based on the total weight of the composition.

According to one embodiment of the present invention, the abrasive cleaning composition does not contain additional calcium carbonate-based materials. Examples of calcium carbonate-based materials are calcium carbonate, calcium carbonate containing minerals, or mixed carbonate based fillers such as calcium associated with magnesium and analogues or derivatives, various matter such as clay or talc or analogues or derivatives, and mixtures of these fillers, such as, for example, talc-calcium carbonate or calcium carbonate-kaolin mixtures, or mixtures of natural calcium carbonate with aluminium hydroxide, mica or with synthetic or natural fibers or co-structures of minerals such as talc-calcium carbonate or talc-titanium dioxide or calcium carbonate-titanium dioxide co-structures.

The abrasive cleaning composition of the present invention may be in form of a solid or in form of a liquid. According to one embodiment, the abrasive cleaning composition is in form of a solid, preferably a powder, a granulate, a tablet, a stick, a chunk, a block, a sponge or a brick. According to another embodiment, the abrasive cleaning composition is in form of a liquid, preferably a solution, a suspension, a paste, an emulsion, a cream, an oil, or a gel.

According to one embodiment of the present invention, the abrasive cleaning composition is a liquid, aqueous composition. According to one embodiment the aqueous composition comprises from 1 to 90 wt.-% water, based on the total weight of the composition, preferably from 5 to 80 wt.-%, more preferably from 10 to 70, and most preferably from 20 to 60 wt.-%.

According to another embodiment of the present invention, the abrasive cleaning composition is a liquid, non-aqueous composition. According to one embodiment the aqueous composition comprises from 1 to 90 wt.-% of a solvent, based on the total weight of the composition, preferably from 5 to 80 wt.-%, more preferably from 10 to 70, and most preferably from 20 to 60 wt.-%. Suitable solvents are known to the skilled person and are, for example, aliphatic alcohols, ethers and diethers having from 4 to 14 carbon atoms, glycols, alkoxylated glycols, glycol ethers, alkoxylated aromatic alcohols, aromatic alcohols, terpenes, natural oils, or mixtures thereof.

According to one embodiment the abrasive cleaning composition is a neutral composition having a pH of 6 to 8, measured at 20° C., preferably from 6.5 to 7.5, and most preferably about 7. According to an alternative embodiment, the abrasive cleaning composition has a pH above 4, measured at 20° C. According to another alternative embodiment, the composition has a pH below 8, measured at 20° C. For example, the abrasive cleaning composition may have a pH from 8 to 11 or from 8 to 10. Means for adjusting the pH are known to the skilled person.

In case the abrasive cleaning composition is in liquid form, it may be a thickened composition having a Brookfield viscosity from 4 000 to 50 000 mPa·s at 20° C.

The abrasive cleaning composition may further comprise a surfactant. According to one embodiment of the present invention, the abrasive cleaning composition comprises from 0.1 to 10 wt.-% of a surfactant, preferably from 0.5 to 8 wt.-%, and most preferably from 1 to 5 wt.-%, based on the total amount of the composition.

Suitable surfactants are known to the skilled person and may be selected from non-ionic, anionic, zwitterionic, amphoteric, cationic surfactants, and mixtures thereof.

Examples of suitable nonionic surfactants are compounds produced by the condensation of simple alkylene oxides, which are hydrophilic in nature, with an aliphatic or alkyl-aromatic hydrophobic compound having a reactive hydrogen atom. Suitable anionic surfactants are, for example, water-soluble salts of organic sulphuric acid mono-esters and sulphonic acids which have in the molecular structure a branched or straight chain alkyl group containing from 6 to 22 carbon atoms in the alkyl part. Examples of suitable zwitterionic surfactants are of aliphatic quaternary ammonium, sulphonium and phosphonium compounds having an aliphatic group of from 8 to 18 carbon atoms and an aliphatic group substituted by an anionic water-solubilising group, for instance betaine and betaine derivatives such as alkyl betaine, in particular $C_{12}$-$C_{16}$ alkyl betaine, 3-(N,N-dimethyl-N-hexadecylammonium)-propane-1-sulphonate betaine, 3-(dodecylmethyl-sulphonium)-propane-1-sulphonate betaine, 3-(cetylmethyl-phosphonium)-propane-1-sulphonate betaine and N,N-dimethyl-N-dodecyl-glycine. Suitable amphoteric surfactants are, for example, derivatives of aliphatic secondary and tertiary amines containing an alkyl group of 8 to 20 carbon atoms and an aliphatic group substituted by an anionic water-solubilising group, for instance sodium 3-dodecylamino-propionate, sodium 3-dodecylaminopropane-sulphonate and sodium N-2-hydroxy-dodecyl-N-methyltaurate. Examples of suitable cationic surfactants are quaternary ammonium salts having one or two alkyl or aralkyl groups of from 8 to 20 carbon atoms and two or three small aliphatic (e.g. methyl) groups, for instance, cetyltrimethylammonium chloride. Further examples are given in well-known text books such as "Household Cleaning, Care and Maintenance Products", Edts. Herrmann G. Hauthal, G. Wagner, 1$^{st}$ Edition, Verlag für Chem. Industrie H. Ziolkowsky 2004, or "Kosmetische Emulsionen and Cremes", Gerd Kutz, Verlag für Chem. Industrie H. Ziolkowsky 2001.

The abrasive composition of the present invention may further comprise ingredients which aid in its cleaning performance. For example, the composition may contain detergent builders and mixtures of such builders in an amount of up to 25 wt.-%, based on the total amount of the composition. Suitable inorganic or organic detergent builders are known to the skilled person and may be selected, for example, from sodium tripolyphosphate or sodium aluminium silicate.

According to one embodiment, in addition to the components already mentioned, the abrasive cleaning composition further comprises dispersing agents, thickeners, preservatives, humectants, foaming agents, fluoride sources, flavouring agents, fragrances, colorants, active agents, and/or buffering systems. Examples of active agents are pharmaceutically, biologically or cosmetically active agents, biocides, or disinfecting agents. The abrasive cleaning composition of the present invention may also comprise further optional ingredients which are not mentioned here but known to skilled person.

The abrasive cleaning composition of the present invention may further comprise a carrier material such as a toothpaste formulation, a chewable gum, a patch, a soap, a cream, or an oil.

The inventors of the present invention surprisingly found that abrasive cleaning composition comprising surface-reacted calcium carbonate as abrasive material provides a very gentle and low abrasiveness. Therefore, the abrasive cleaning composition of the present invention is suitable for cleaning delicate surfaces, which may be most likely damaged by the conventional calcium carbonate based abrasives, such as automotive paint, ceramic cook tops, car dashboards, bathroom fittings, sensitive teeth or teeth of children.

According to one preferred embodiment the abrasive cleaning composition of the present invention is an oral care composition. Preferably the abrasive cleaning composition is a toothpaste, a toothpowder, a powder for dental powder blasting, or a chewable gum, and more preferably a toothpaste.

In case the abrasive cleaning composition is an oral care composition, the surface-reacted calcium carbonate may be a reaction product of natural or synthetic calcium carbonate with carbon dioxide and phosphoric acid. The surface-reacted calcium carbonate can consist of one type of surface-reacted calcium carbonate or can be a mixture of two or more types of surface-reacted calcium carbonate.

According to a preferred embodiment of the present invention, the abrasive cleaning composition is a toothpaste and the surface-reacted calcium carbonate is a reaction product of natural or synthetic calcium carbonate with carbon dioxide and phosphoric acid. The toothpaste may have a pH between 8 and 10.

According to one embodiment, the toothpaste comprises from 10 to 80 wt.-%, preferably from 15 to 70 wt.-%, more preferably from 20 to 60 wt.-%, even more preferably from 25 to 50 wt.-%, and most preferably about 30 wt.-% of the surface-reacted calcium carbonate, based on the total weight of the toothpaste.

The toothpaste of the present invention may contain the surface-reacted calcium carbonate as the only abrasive material. According to another embodiment, the toothpaste of the present invention further comprises at least one additional abrasive material. The at least one additional abrasive material may be selected from the additional abrasive materials defined above. Preferably, the at least one additional abrasive material is selected from the group consisting of natural calcium carbonate, precipitated calcium carbonate, aluminium hydroxide, calcium hydrogen phosphate, silica, hydroxylapatite, and mixtures thereof.

According to one embodiment of the present invention, the abrasive cleaning composition is a toothpaste comprising at least 6 wt.-%, based on the total weight of the toothpaste, of a surface-reacted calcium carbonate with carbon dioxide and at least one acid, preferably phosphoric acid. According to another embodiment of the present invention, the abrasive cleaning composition is a toothpaste comprising at least 6 wt.-%, based on the total weight of the toothpaste, of a surface-reacted calcium carbonate with carbon dioxide and at least one acid, preferably phosphoric acid, and from 1 to 80 wt.-% of an additional abrasive material, preferably selected from the group consisting of natural calcium carbonate, precipitated calcium carbonate, aluminium hydroxide, calcium hydrogen phosphate, silica, hydroxylapatite, and mixtures thereof.

According to one embodiment of the present invention, the abrasive cleaning composition is an oral care composition and the abrasive materials included in the oral care composition have a radioactive dentin abrasion (RDA) value between 10 and 100, preferably between 30 and 70. According to one embodiment of the present invention, the abrasive cleaning composition is an oral care composition and the surface-reacted calcium carbonate included in the oral care composition has a radioactive dentin abrasion (RDA) value between 10 and 100, preferably between 30 and 70. According to another embodiment of the present invention, the abrasive cleaning composition is a toothpaste and the surface-reacted calcium carbonate included in the toothpaste has a radioactive dentin abrasion (RDA) between 10 and 100, preferably between 30 and 70. According to one embodiment of the present invention, the toothpaste is a toothpaste for sensitive teeth and/or for children's teeth, and preferably the surface-reacted calcium carbonate has an RDA between 30 and 70, and most preferably between 30 and 50.

In addition to the abrasive material, the oral care composition may further comprise fluoride compounds, surfactants, binders, humectants, remineralizers, flavouring agents, sweetening agents and/or water.

Examples of suitable fluoride compounds are sodium fluoride, stannous fluoride, sodium monofluorophosphate, potassium fluoride, potassium stannous fluoride, sodium fluorostannate, stannous chlorofluoride and amine fluoride. The fluoride compounds may be added in an amount from 0.1 to 2 wt.-%, based on the total weight of the oral care composition. Good results can be achieved employing an amount of fluoride compound to provide available fluoride ion in the range of 300 to 2 000 ppm in the toothpaste, preferably about 1 450 ppm.

Suitable surfactants are generally anionic organic synthetic surfactants throughout a wide pH range. Representative of such surfactants used in the range of about 0.5 to 5 wt.-%, based on the total weight of the oral care composition, are water-soluble salts of $C_{10}$-$C_{18}$ alkyl sulphates, such as sodium lauryl sulphate, of sulphonated monoglycerides of fatty acids, such as sodium monoglyceride sulphonates, of fatty acid amides of taurine, such as sodium N-methyl-N-palmitoyltauride, and of fatty acid esters of isethionic acid, and aliphatic acylamides, such as sodium N-lauroyl sarcosinate. However, surfactants obtained from natural sources such as cocamidopropyl betaine may also be used.

Suitable binders or thickening agents to provide the desired consistency are, for example, hydroxyethylcellulose, sodium carboxymethylcellulose, natural gums, such as gum karaya, gum arabic, gum tragacanth, xanthan gum or cellulose gum, colloidal silicates, or finely divided silica. Generally, from 0.5 to 5 wt.-%, based on the total weight of the toothpaste composition, can be used.

Various humectants known to the skilled person can be used, such as glycerine, sorbitol and other polyhydric alcohols, for example, in an amount from 20 to 40 wt.-%, based on the total weight of the oral care composition. Examples of suitable flavouring agents include oil of wintergreen, oil of spearmint, oil of peppermint, oil of clove, oil of *sassafras* and the like. Saccharin, aspartame, dextrose, or levulose can be used as sweetening agents, for example, in an amount from 0.01 to 1 wt.-%, based on the total weight of the oral care composition. Preservatives such as sodium benzoate may be present in an amount from 0.01 to 1 wt.-%, based on the total weight of the oral care composition. Colorants such as titanium dioxide may also be added to the oral care composition, for example, in an amount from 0.01 to 1 wt.-%, based on the total weight of the oral care composition.

According to one embodiment of the present invention, the toothpaste is produced by a method comprising the following steps:
  i) providing a mixture of water and a humectants, and optionally at least one of a thickener, a preservative, a fluoride, and a sweetener,
  ii) adding a surface-reacted calcium carbonate, and optionally a colorant, to the mixture of step i), wherein the surface-reacted calcium carbonate is a reaction product of natural or synthetic calcium carbonate with carbon dioxide and at least one acid,
  iii) adding a surfactant to the mixture of step ii), and
  iv) optionally, adding a flavouring agent to the mixture of step iii),
  wherein optionally an additional abrasive material is added after step ii) and before step iii).

However, the toothpaste of the present invention may also be produced by any other method known to the skilled person.

According to a further aspect of the present invention, the abrasive cleaning composition of the present invention is used for cleaning a surface.

According to a further aspect of the present invention, a method for cleaning a surface is provided, wherein the surface is contacted with an abrasive cleaning composition according to the present invention. The surface may be contacted with the inventive composition by applying the composition to the surface, for example, by spraying, pouring or squeezing. The abrasive cleaning composition may be applied to the surface by using an appropriate means such as a mop, a paper towel, a brush, or a cloth, soaked in the composition, which can be in neat or in diluted form.

According to one embodiment of the present invention, the surface is an inanimate surface, preferably selected from the group consisting of household hard surfaces, dish surfaces, leather surfaces, and automotive vehicle surfaces. Examples of household hard surfaces are refrigerators, freezers, washing machines, automatic dryers, ovens, microwave ovens, ceramic cook tops, bathroom fittings or dishwashers. Examples of dish surfaces are dishes, cutlery, cutting boards, or pans.

According to another embodiment of the present invention, the surface is an animate surface, preferably selected from the group consisting of human skin, animal skin, human hair, animal hair, and tissues of the oral cavity such as teeth, gums, tongue or buccal surfaces.

According to one embodiment of the present invention, the method of the present invention further comprises a step of rinsing the composition.

The scope and interest of the present invention will be better understood based on the following figures and examples which are intended to illustrate certain embodiments of the present invention and are non-limitative.

EXAMPLES

1. Measurement Methods

In the following, measurement methods implemented in the examples are described.

Particle Size Distribution

The particle size distribution of the abrasive material particles was measured using a Sedigraph 5100 from the company Micromeritics, USA. The method and the instrument are known to the skilled person and are commonly used to determine grain size of fillers and pigments. The measurement was carried out in an aqueous solution comprising 0.1 wt.-% $Na_4P_2O_7$. The samples were dispersed using a high speed stirrer and supersonics. For the measurement of dispersed samples, no further dispersing agents were added.

pH Value

The pH of a suspension was measured at 25° C. using a Mettler Toledo Seven Easy pH meter and a Mettler Toledo InLab® Expert Pro pH electrode. A three point calibration (according to the segment method) of the instrument was first made using commercially available buffer solutions having pH values of 4, 7 and 10 at 20° C. (from Sigma-Aldrich Corp., USA). The reported pH values are the endpoint values detected by the instrument (the endpoint was when the measured signal differed by less than 0.1 mV from the average over the last 6 seconds).

Relative Radioactive Dentin Abrasion (RDA)

The relative RDA of an abrasive material was determined by using a modified washability and scrub resistance tester (Model 494, Erichsen GmbH & Co. KG, Germany) equipped with a toothbrush head and a Plexiglas surface mounted on a stainless steel plate. The toothbrush head was brushing 5000 times the Plexiglas surface, which was covered with a slurry containing abrasive cleansing particles as e.g. calcium carbonate or silica. The abrasion on the Plexiglas plates was evaluated by measuring the roughness of the surface and the depth of the scratches caused by the abrasive particles. For the measurement, an electron microscopy was used. 10 measurements were carried out per plate. The measurement points were randomly selected.

For application of the slurry on the Plexiglas surface, a peristaltic pump was used to pump 200 g slurry (mixture of 15% abrasive material and a saliva replacement without enzymes) in a loop. The setting of the pump was 30, which corresponded to a pumped volume of approx. 200 ml water per minute. A silicone tube with an inner diameter of 6 mm was used. The machine was angled such that the direction for the outlet in respect to the stainless steel sample mounting plate was at an inclination of 2%, in order to have a proper slurry flow.

Five plates of Plexiglas were placed in the middle of the stainless steel plate and fixed on the sides using tape (Plexiglas GS, 3 mm thickness, colour: orange 2C04, pre-cut to a size of 80 mm×80 mm). Five plates were necessary to ensure always the same height for the brushes brushing the surface. Only the plate in the middle (number 3) was used for the final evaluation of the abrasion. The other plates were just used to adjust the height, and so they could be used several times.

A toothbrush head (Paro, Switzerland) was placed above the middle of the stainless steel plate. All bristles of the toothbrush had the same length, were rounded and made of nylon. The fixture itself was made of stainless steel and had, including the toothbrush head, a total weight of approx. 157 g.

To quantify and qualify the abrasion of the tested calcium carbonate particles, it was necessary to establish a calibration curve. To generate such a curve, the abrasion of a placebo was measured first, which was just the saliva mixture without cleansing particles. This test also took the influence of the toothbrush on the abrasion into consideration. In addition, the abrasion using the aforementioned system was measured for two silicas (Sorbosil AC 39 and Sorbosil AC 33), which are both well documented and established abrasives in the toothpaste industry. Their officially measured abrasion values (RDA) are published and known. The abrasion values obtained by the measurement described herein were then related to the published data, which made it possible to compare the data from the herein described measurements with the values obtained by the official standard method ISO 11609.

The calibration curves started with the placebo at abrasion=0 and went stepwise up to an abrasion value of 180, wherein Sorbosil AC 39 had a value of 105 and Sorbosil AC 33 a value of 180.

Brookfield Viscosity

The Brookfield viscosity of the abrasive material particles suspension or abrasive cleaning composition was measured after one hour of production and after one minute of stirring at 20° C.±2° C. at 100 rpm by the use of a Brookfield viscometer type RVT equipped with an appropriate disc spindle, for example spindle 2 to 5.

Gloss Measurement

The gloss measurements were carried out with the haze meter "Haze-Gloss" (BYK Gardener GmbH, Germany).

2. Materials

MCC1: A blend of 100 parts surface-reacted calcium carbonate, based on GCC1 and phosphoric acid, and 20 parts GCC2. Properties: $d_{50}$=8.6 μm, $d_{98}$=20.2 μm, relative RDA=37, low level of abrasion.

MCC2: surface-reacted calcium carbonate based on GCC2 and phosphoric acid. Properties: $d_{50}$=6.3 μm, $d_{98}$=15.8 μm, relative RDA=11, very low level of abrasion.

MCC3: surface-reacted calcium carbonate based on GCC1 and phosphoric acid. Properties: $d_{50}$=6.5 μm, $d_{98}$=16.8 μm, relative RDA=61, medium level of abrasion.

MCC4: surface-reacted calcium carbonate based on GCC1 and phosphoric acid. Properties: $d_{50}$=3.8 μm, $d_{98}$=11.0 μm, relative RDA=23, low level of abrasion.

GCC1: natural ground calcium carbonate obtained from Orgon limestone. Properties: $d_{50}$=3 μm, $d_{98}$=12, relative RDA=81, medium level of abrasion.

GCC2: natural ground calcium carbonate obtained from Avenza marble. Properties: $d_{50}$=1.7 μm, $d_{98}$=8.0, relative RDA=100, high level of abrasion.

GCC3: natural ground calcium carbonate obtained from Avenza marble. Properties: $d_{50}$=8.86 μm, $d_{98}$=50.0 μm.

3. Examples

Example 1

Toothpaste Compositions

Toothpaste samples 1 to 6 were produced according to the following procedure using the ingredients and amounts compiled in Table 1 below.

Step A: Water and sorbitol were mixed in a beaker. Xanthan gum, sodium benzoate, fluorophosphate (phoskadent Na 211, BK Guilini, Germany) and sodium saccharine were mixed and the obtained mixture was added to the beaker.

Step B: Surface-reacted calcium carbonate and titanium dioxide were wetted with water and subsequently added to the mixture of step A. The mixture was homogenized until a smooth mixture was obtained.

Step C: The silica Sorbosil TC 15 (PQ Corporation, USA) was added to the mixture of step B under homogenizing conditions, whereby the mixture was heating up strongly. The mixture was stirred until it was cooled down to room temperature.

Step D: The surfactant sodium lauryl sulphate was added in form of a 25% solution to the mixture of step C under slow agitation.

Step E: 0.8 wt.-% (2.4 g) spearmint flavour was added to the mixture of step D.

The phase stability was evaluated by visual inspection, and the pH value measurements were carried out as described above. The mouthfeel was evaluated by brushing teeth with the toothpaste samples. The samples were tested on the day of production. The results are compiled in Table 2 below, which shows that all samples were stable and had a good texture and a smooth surface. Furthermore, all samples had an acceptable pH.

TABLE 1

Ingredients and amounts of toothpaste samples 1 to 6. The percentages refer to weight percentages based on the total weight of the composition.

| Ingredients | Sample 1 | Sample 2 | Sample 3 | Sample 4 | Sample 5 | Sample 6 |
| --- | --- | --- | --- | --- | --- | --- |
| Sorbitol 70% | 28.0% | 28.0% | 25.0% | 30.0% | 31.0% | 31.0% |
|  | (84.0 g) | (84.0 g) | (75.0 g) | (90.0 g) | (93.0 g) | (93.0 g) |
| Water | 34.3% | 32.8% | 32.3% | 27.4% | 30.0% | 30.0% |
|  | (102.9 g) | (98.4 g) | (96.9 g) | (82.2 g) | (90.0 g) | (90.0 g) |

TABLE 1-continued

Ingredients and amounts of toothpaste samples 1 to 6. The percentages refer to weight percentages based on the total weight of the composition.

| Ingredients | Sample 1 | Sample 2 | Sample 3 | Sample 4 | Sample 5 | Sample 6 |
|---|---|---|---|---|---|---|
| Phoskadent Na 211 | 1.1% (3.3 g) | 1.1% (3.3 g) | 1.1% (3.3 g) | 1.1% (3.3 g) | 1.1% (3.3 g) | 1.1% (3.3 g) |
| Xanthan gum | 0.8% (2.4 g) | 0.8% (2.4 g) | 0.8% (2.4 g) | 0.8% (2.4 g) | 0.8% (2.4 g) | 0.8% (2.4 g) |
| Sodium saccharin | 0.1% (0.3 g) | 0.1% (0.3 g) | 0.1% (0.3 g) | 0.2% (0.6 g) | 0.1% (0.3 g) | 0.1% (0.3 g) |
| Sodium benzoate | 0.2% (0.6 g) | 0.2% (0.6 g) | 0.2% (0.6 g) | — | — | — |
| MCC 1 | — | — | 35.0% (105.0 g) | — | — | — |
| MCC 2 | 30.0% (90.0 g) | — | — | 35.0% (105.0 g) | — | — |
| MCC 3 | — | 30.0% (90.0 g) | — | — | 30.0% (90.0 g) | — |
| MCC 4 | — | — | — | — | — | 30.0% (90.0 g) |
| Titanium dioxide | 0.5% (1.5 g) | 2.0% (6.0 g) | 0.5% (1.5 g) | 0.5% (1.5 g) | 2.0% (6.0 g) | 2.0% (6.0 g) |
| Sorbosil TC 15 | 3.0% (9.0 g) | 3.0% (9.0 g) | 3.0% (9.0 g) | 3.0% (9.0 g) | 3.0% (9.0 g) | 3.0% (9.0 g) |
| Sodium lauryl sulphate (25% solution) | 2.0% (6.0 g) | 2.0% (6.0 g) | 2.0% (6.0 g) | 2.0% (6.0 g) | 2.0% (6.0 g) | 2.0% (6.0 g) |

TABLE 2

Results obtained for samples 1 to 6.

| | Sample 1 | Sample 2 | Sample 3 | Sample 4 | Sample 5 | Sample 6 |
|---|---|---|---|---|---|---|
| Phase stability | Stable | Stable | Stable | Stable | Stable | Stable |
| pH | 8.57 | 8.45 | 8.85 | 8.65 | 8.51 | 8.4 |
| Appearance/ mouthfeel | Good texture, smooth surface, a little liquid | Good texture, smooth surface, a little liquid | Good texture, smooth surface, a little liquid | Good texture, smooth surface | Good texture, smooth surface | Good texture, smooth surface, a little liquid |

Example 2

Toothpaste Compositions

Toothpaste samples 7 to 9 were produced according to the following procedure using the ingredients and amounts compiled in Table 3 below.

Step A: Water, sorbitol, fluorophosphate (phoskadent Na 211, BK Guilini, Germany), cellulose gum (Akucell AF 2985, AkzoNobel N.V., The Netherlands), and sweetener (Sunett®, Celanese Corp., USA) were mixed in a beaker.

Step B: Surface-reacted calcium carbonate and titanium dioxide were wetted with water and subsequently added to the mixture of step A. The mixture was homogenized until a smooth mixture was obtained.

Step C: The silica Sorbosil TC 15 (PQ Corporation, USA) was added to the mixture of step B under homogenizing conditions, whereby the mixture was heating up strongly. The mixture was stirred until it was cooled down to room temperature.

Step D: The surfactant Tego Betaine ZF (Evonik Industries AG, Germany) was added in form of a 25% solution to the mixture of step C under slow agitation.

Step E: 0.8 wt.-% (2.4 g) spearmint flavour was added to the mixture of step D.

Figure 1:
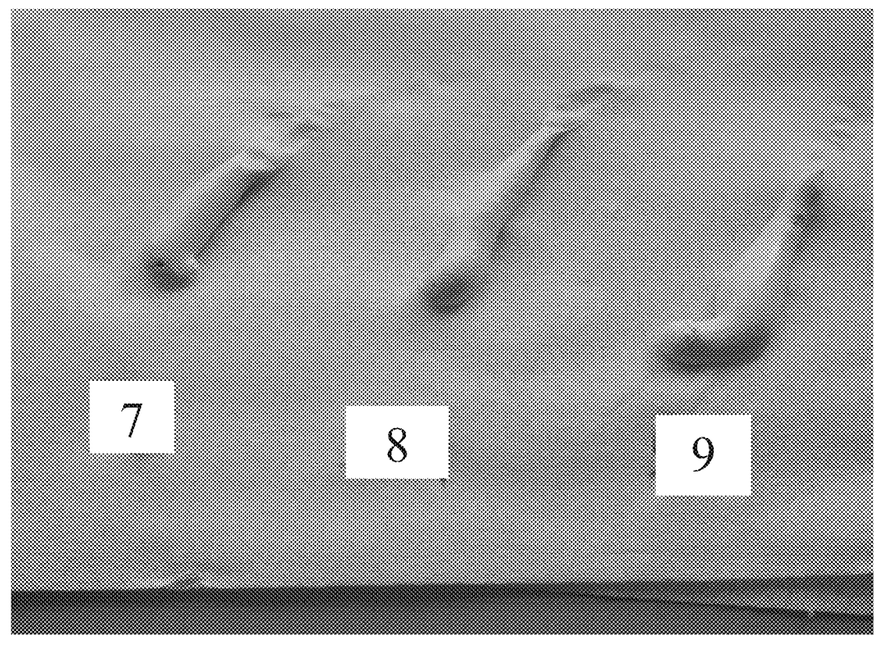
FIG. 1 shows a photograph of toothpaste samples according to the present invention, which were applied to a paper cloth on the day of production.

The phase stability was evaluated by visual inspection, and the pH value measurements were carried out as described above. The mouthfeel was evaluated by brushing teeth with the toothpaste samples. The samples were tested on the day of production, after 6 weeks, 12 weeks, 6 months and 12 months. The results are compiled in Tables 4 to 6 below, which show that all samples were stable and had a good texture and a smooth surface. Furthermore, all samples had an acceptable pH, even after a long storage period. FIG. 1 presents a photograph of samples 7 to 9 applied to a paper cloth on the day of production, which shows that the texture of the samples is very smooth and cream-like.

TABLE 3

Ingredients and amounts of toothpaste samples 7 to 9. The percentages refer to weight percentages based on the total weight of the composition.

| Ingredients | Sample 7 | Sample 8 | Sample 9 |
|---|---|---|---|
| Sorbitol 70% | 35.0% (105.0 g) | 35.0% (105.0 g) | 25.0% (75.0 g) |
| Water | 27.6% (82.8 g) | 26.1% (78.3 g) | 36.1% (108.3 g) |
| Phoskadent Na 211 | 1.1% (3.3 g) | 1.1% (3.3 g) | 1.1% (3.3 g) |

TABLE 3-continued

Ingredients and amounts of toothpaste samples 7
to 9. The percentages refer to weight percentages
based on the total weight of the composition.

| Ingredients | Sample 7 | Sample 8 | Sample 9 |
|---|---|---|---|
| Akucell AF 2985 | 0.7% (2.1 g) | 0.7% (2.1 g) | 0.7% (2.1 g) |
| Sunett ® | 0.1% (0.3 g) | 0.1% (0.3 g) | 0.1% (0.3 g) |
| MCC 4 | 30.0% (90.0 g) | 30.0% (90.0 g) | 30.0% (90.0 g) |
| Titanium dioxide | 0.5% (1.5 g) | 2.0% (6.0 g) | 2.0% (6.0 g) |
| Sorbosil TC 15 | 3.0% (9.0 g) | 3.0% (9.0 g) | 3.0% (9.0 g) |
| Tego Betaine ZF | 2.0% (6.0 g) | 2.0% (6.0 g) | 2.0% (6.0 g) |

TABLE 4

Results obtained for sample 7.

| | production day | 6 weeks | 12 weeks | 6 months | 12 months |
|---|---|---|---|---|---|
| Phase stability | Stable | Stable | Stable | Stable | Stable |
| pH | 8.58 | 8.63 | 8.64 | 8.75 | 8.83 |
| Appearance/mouthfeel | Good texture | Good texture | Good texture | Good texture | Good texture |

TABLE 5

Results obtained for sample 8.

| | production day | 6 weeks | 12 weeks | 6 months | 12 months |
|---|---|---|---|---|---|
| Phase stability | Stable | Stable | Stable | Stable | Stable |
| pH | 8.37 | 8.61 | 8.61 | 8.7 | 8.78 |
| Appearance/mouthfeel | Smooth, good texture, cream-like texture | Smooth, good texture, cream-like texture | Smooth, good texture, cream-like texture | Smooth, good texture, cream-like texture | Smooth, good texture, cream-like texture |

TABLE 6

Results obtained for sample 9.

| | production day | 6 weeks | 12 weeks | 6 months | 12 months |
|---|---|---|---|---|---|
| Phase stability | Stable | Stable | Stable | Stable | Stable |
| pH | 8.44 | 8.5 | 8.52 | 8.65 | 8.72 |
| Appearance/mouthfeel | Smooth, very good texture, cream-like texture | Smooth, very good texture, cream-like texture | Smooth, very good texture, cream-like texture | Smooth, very good texture, cream-like texture | Smooth, very good texture, cream-like texture |

Example 3

Scouring Cream

Scouring cream samples 10 to 12 were produced according to the following procedure using the ingredients and amounts compiled in Table 7 below.

Step 1: Water and a thickener (Rheosolve 633, Coatex SAS, France) were added to a beaker fitted with an agitator (speed: 380 rpm). The pH was adjusted between 10 and 11 using sodium hydroxide (50% solution).

Step 2: The surface-reacted calcium carbonate or ground calcium carbonate (as comparative example) was added stepwise to the mixture of step 1 under high agitation (speed 2, 250-300 rpm). The mixture was stirred until it was homogeneous.

Step 3: A cocoglycoside surfactant (Plantacare 818 UP, BASF, Germany) was added in form of a 20% solution to the homogeneous mixture of step 2. Subsequently, lemon essential oil and Polysorbate 60 were added under slow stirring (speed 1, 70 rpm).

TABLE 7

Ingredients and amounts of scouring cream samples
10 to 12. The percentages refer to weight percentages
based on the total weight of the composition.

| Ingredients | Sample 10 (comparative) | Sample 11 | Sample 12 |
|---|---|---|---|
| Water | add. 100 | add. 100 | add. 100 |
| Rheosolve 633 | 0.85 wt.-% | 0.85 wt.-% | 0.85 wt.-% |
| Sodium hydroxide (50% solution) | 0.13 wt.-% | 0.13 wt.-% | 0.13 wt.-% |
| GCC3 | 50 wt.-% | — | — |
| MCC1 | — | 50 wt.-% | — |
| MCC2 | — | — | 50 wt.-% |
| Plantacare 818 UP (20% solution) | 5 wt.-% | 5 wt.-% | 5 wt.-% |
| Lemon essential oil | 0.1 wt.-% | 0.1 wt.-% | 0.1 wt.-% |
| Tween 60V Pharma | 0.2 wt.-% | 0.2 wt.-% | 0.2 wt.-% |

The abrasion of the obtained scouring cream samples was tested within 24 h at a temperature of 23° C. according to the following procedure:

The abrasion was determined by using a washability and scrub resistance tester (Model 494, Erichsen GmbH & Co. KG, Germany) equipped with a fastening with plastic plate to fix a cloth (Erichsen GmbH & Co. KG, Germany). Three weights (400 g) were fixed on the fastening so that the fastening including the weights and the plate had a weight of about 580 g. A cloth square (size: 9×9.1 cm) was fixed on the plastic plate with an adhesive (Scotch$^{3M}$) tape and was put in the notches of the fastening.

In the tester, a glass plate was fixed in a horizontal position in the space provided for this purpose. A Plexiglas plate (size: 4 cm×30 cm, Steba Kunststoffe AG, Swiss) was taped with adhesive Scotch tape on the glass plate. The distance between the top of the tray and the plate was about 3.9 cm and between the bottom of the tray and the plate about 4.5 cm. 2 g water was added on the cloth fixed on the fastening. 25 g scouring agent were added onto the Plexiglas plate. The fastening was positioned on the Plexiglas plate with the tension cable. The testing machine was set to 200 cycles and started. At the end of the test, the Plexiglas plate was removed and rinsed. The frame of the machine and the glass plate were cleaned with hot water, followed by deionized water. Every sample was tested three times.

The abrasion of the scouring cream samples was determined by measuring the gloss of the Plexiglas plate at 20° using the haze meter "Haze-Gloss" (BYK Gardener GmbH, Germany). The measurement was carried out at 8 different points in the centre of the plate by slightly moving the plate left to right and from top to bottom. The average gloss value for every sample is given in Table 8 below. The abrasiveness of a sample was calculated by subtracting the average gloss value measured for the Plexiglas plate that has been treated with the respective sample from the average gloss value measured for the untreated Plexiglas plate. The abrasion value and level for every sample is given in Table 8 below.

TABLE 8

Results obtained for scouring cream samples 10 to 12.

|  | Untreated Plexiglas plate | Sample 10 (comparative) | Sample 11 | Sample 12 |
|---|---|---|---|---|
| Abrasion value | — | 16.2 | 4.5 | 2.5 |
| Abrasion level | — | medium | low | low |
| Gloss value | 77.5 | 61.3 | 73 | 75 |
| Gloss level | — | — | low | very high | very high |

It can be gathered from Table 8 that the abrasive cleaning compositions including the surface-reacted calcium carbonate abrasive according to the present invention had a lower abrasion value and caused lower damage to the cleaned surface (indicated by the higher gloss value) compared to the comparative example cleaning composition containing the ground calcium carbonate.

The invention claimed is:

1. An abrasive household surface cleaning composition comprising:
   25 to 80 wt.-%, based on the total weight of the composition, of a surface-reacted calcium carbonate as an abrasive material, wherein the surface-reacted calcium carbonate is a reaction product of natural or synthetic calcium carbonate with carbon dioxide and at least one acid, the surface-reacted calcium carbonate comprises an insoluble, at least partially crystalline calcium salt of an anion of the at least one acid which is formed on the surface of the natural or synthetic calcium carbonate; and
   from 0.1 to 10 wt.-%, based on the total weight of the composition, of a surfactant chosen from a non-ionic surfactant, a zwitterionic surfactant, an amphoteric surfactant, a cationic surfactant, a water-soluble salt of a C10-C18 alkyl sulphate, sodium lauryl sulphate, a sulphonated monoglyceride of a fatty acid, sodium monoglyceride sulphonate, a fatty acid amide of taurine, sodium N-methyl-N-palmitoyltauride, a fatty acid ester of isethionic acid, an aliphatic acylamide, sodium N-lauroyl sarcosinate, cocamidopropyl betaine, and any mixture thereof
   wherein the household surface cleaning composition is in the form of a liquid comprising a cream.

2. The composition according to claim 1, wherein the composition further comprises at least one additional abrasive material.

3. The composition according to claim 2, wherein the at least one additional abrasive material is selected from the group consisting of silica, precipitated silica, alumina, aluminosilicate, metaphosphate, tricalcium phosphate, calcium pyrophosphate, natural ground calcium carbonate, precipitated calcium carbonate, sodium bicarbonate, bentonite, kaolin, aluminium hydroxide, calcium hydrogen phosphate, hydroxylapatite, and any mixture thereof.

4. The composition according to claim 1, wherein the at least one acid is selected from the group consisting of hydrochloric acid, sulphuric acid, sulphurous acid, phosphoric acid, citric acid, oxalic acid, acetic acid, formic acid, and any mixture thereof.

5. The composition according to claim 1, wherein the at least one acid is phosphoric acid.

6. The composition according to claim 1, wherein the surface-reacted calcium carbonate is in form of particles having a weight median particle size $d_{50}$ from 0.1 to 100 μm.

7. The composition according to claim 1, wherein the surface-reacted calcium carbonate is in form of particles having a weight median particle size $d_{50}$ from 0.5 to 50 μm.

8. The composition according to claim 1, wherein the surface-reacted calcium carbonate is in form of particles having a weight median particle size $d_{50}$ from 1 to 20 μm.

9. The composition according to claim 1, wherein the surface-reacted calcium carbonate is in form of particles having a weight median particle size $d_{50}$ from 2 to 10 μm.

10. The composition according to claim 1, wherein the surface-reacted calcium carbonate is in form of particles having a weight median particle size $d_{50}$ from 5 to 10 μm.

11. The composition according to claim 1, wherein the composition is a household hard surface cleaner for cleaning refrigerators, freezers, washing machines, dryers, ovens, ceramic cook tops, bathroom fittings, dish washers, dishes, cutlery, cutting boards, pans or automobiles.

12. The composition according to claim 1, wherein the composition does not contain additional calcium carbonate-based materials.

13. The composition according to claim 1, wherein the surfactant is present in an amount from 1 to 5 wt.-%, based on the total amount of the composition.

14. The composition according to claim 1, wherein the surfactant is selected from group consisting of a water-soluble salt of a C10-C18 alkyl sulphate, sodium lauryl sulphate, a sulphonated monoglyceride of a fatty acid, sodium monoglyceride sulphonate, a fatty acid amide of taurine, sodium N-methyl-N-palmitoyltauride, a fatty acid ester of isethionic acid, an aliphatic acylamide, sodium N-lauroyl sarcosinate, and cocamidopropyl betaine.

15. The composition according to claim 1, which further comprises a solvent.

16. The composition according to claim 15, wherein the solvent is selected from the group consisting of an aliphatic alcohol, an ether having from 4 to 14 carbon atoms, a di ether having from 4 to 14 carbon atoms, a glycol, an alkoxylated glycol, a glycol ether, an alkoxylated aromatic alcohol, an aromatic alcohol, a terpene, a natural oil, and any mixture thereof.

17. The composition according to claim 1, which further comprises a detergent builder.

18. The composition according to claim 17, wherein the detergent builder is sodium tripolyphosphate or sodium aluminium silicate.

19. The composition according to claim 1, wherein the composition further comprises one or more dispersing agents, thickeners, preservatives, foaming agents, fragrances, colorants, biocides, disinfecting agents, and buffeting systems.

20. The composition according to claim 1, wherein the composition further comprises a solvent, a detergent builder, and one or more dispersing agents, thickeners, preservatives, foaming agents, fragrances, colorants, biocides, disinfecting agents, and buffering systems.

21. The composition according to claim 1, wherein the surface-reacted calcium carbonate is a reaction product of natural calcium carbonate with carbon dioxide and at the least one acid.

22. The composition according to claim 21, wherein the at least one acid is phosphoric acid.

23. The composition according to claim 1, having a pH of from 10 to 11.

24. The composition according to claim 1, wherein the surface-reacted calcium carbonate has a specific surface area of from 5 $m^2/g$ to 200 $m^2/g$.

25. The composition according to claim 1, further comprising from 0.5 to 5 wt.-% of a thickener based on the total weight of the composition.

26. The composition according to claim 25, wherein the thickener comprises hydroxyethylcellulose, sodium carboxymethylcellulose, gum karaya, gum arabic, gum tragacanth, xanthan gum, cellulose gum, colloidal silicate, or a mixture thereof.

* * * * *